United States Patent [19]

Horn

[11] Patent Number: 5,071,529
[45] Date of Patent: Dec. 10, 1991

[54] METHOD AND APPARATUS FOR BONDING A POLYPEPTIDE TO A MACROMOLECULAR SUPPORT BY PHOTOLYTIC CATALYSIS

[75] Inventor: Marcus J. Horn, Arlington, Mass.

[73] Assignee: Hewlett-Packard Company, Palo Alto, Calif.

[21] Appl. No.: 230,597

[22] Filed: Aug. 10, 1988

[51] Int. Cl.$^5$ ................................. C08L 1/00
[52] U.S. Cl. ................................. 204/157.6
[58] Field of Search ........................ 204/157.6

[56] References Cited

U.S. PATENT DOCUMENTS 4,039,413  8/1977  Kraemer ............... 204/159.12
4,451,568  5/1984  Schneider .............. 435/181

OTHER PUBLICATIONS

Laursen et al., "Coupling Methods and Strategies in Solid-Phase Sequencing", *Molecular Biology, Biochemistry and Biophysies*, vol. 25, (1977), pp. 21 and 29-31.

Primary Examiner—John F. Niebling
Assistant Examiner—Isabelle Rodriguez

[57] ABSTRACT

A method for immobilizing proteins and large polypeptides on a carrier support for solid-phase sequence. Upon irradiation, a functional group bound to the carrier is excited to a triplet biradical state and thereby rendered capable of bonding to amino acid units; unbound functional groups return to their starting state upon removal of the radiation.

9 Claims, 4 Drawing Sheets

COMPARISON OF SEQUENCEABLE AMINO ACID RECOVERY
(CYT. C SEQUENCE: PAPFEQGSAK...)

| METHOD | $P_1$ | $A_2$ | $P_3$ | $F_4$ | $A_9$ | $K_{10}$ |
|---|---|---|---|---|---|---|
| DITC GLASS | 0 | 1 | 1 | 1 | 1 | 0 |
| 10m FLASH | .71 | .88 | 1.0 | 1.0 | .67 | .83 |
| 40m FLASH | .71 | .38 | .40 | .27 | .54 | .72 |

FIG 3

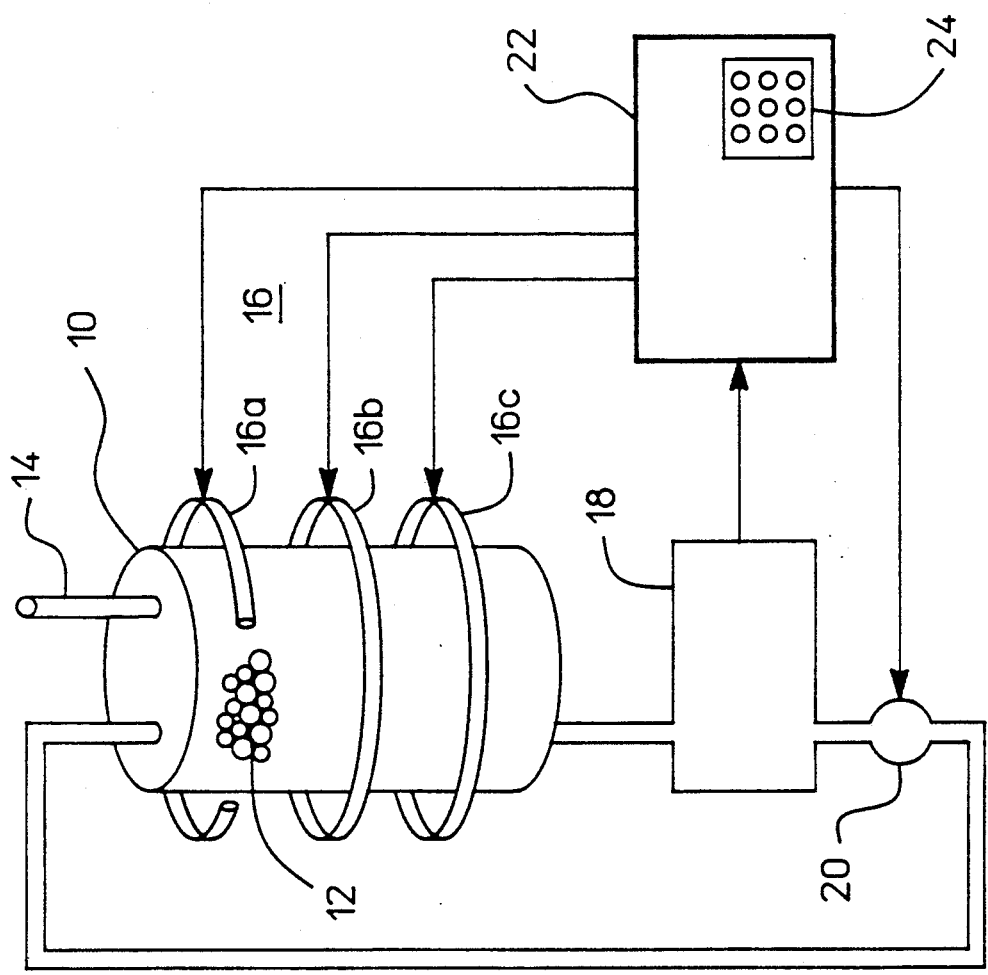

METHOD AND APPARATUS FOR BONDING A POLYPEPTIDE TO A MACROMOLECULAR SUPPORT BY PHOTOLYTIC CATALYSIS

BACKGROUND OF THE INVENTION

A. Field of the Invention

This invention relates to a method for sequential analysis of polypeptides and proteins, and, more specifically, a photochemical method for binding polypeptides and proteins to a carrier in order to facilitate sequential analysis.

B. Prior Art

Recent advances in medical and pharmaceutical technology have uncovered a wide range of therapeutic uses for short- and long-chain polypeptide molecules. These substances, which are composed of a chain of linked amino acid molecules, control or participate in virtually all phases of cellular activity and structure. Direct control over specific metabolic levels or molecular characteristics of physiologically active polypeptides has been employed to achieve highly localized treatment of a variety of disorders, as well as promotion of desirable traits in commercial livestock. However, despite the significant potential for beneficial use of biologically active polypeptides, their size and structural complexity greatly limit the ability of scientists to understand and predict behavior in living systems.

A basic starting point for analysis of any linear chain polypeptide is determination of the precise sequence of its individual amino acid units. Researchers currently employ a variety of sequencing methodologies, the most common being the Edman degradation. In this method, successive amino acids are removed from the end of the chain by reacting the N-terminal amino acid residue with a reagent which allows selective removal of that residue. The resulting amino acid derivative is converted into a stable compound which can be chemically removed from the reaction mixture and identified.

Edman degradation and similar sequencing methods are commonly performed on a polypeptide immobilized on a solid support. This method of facilitating iterative amino acid cleavage offers a number of advantages. Assuming covalent bonding of the sample molecules to the carrier, virtually all of the sample will remain bound notwithstanding application of organic and aqueous solvents, salts or detergents. Hence, it is possible to achieve accurate sequence analysis even at picomole polypeptide levels. Furthermore, once attachment of the polypeptide has taken place, the Edman process will generally take place with a high degree of reliability.

After the sample has been bound to the solid support, the various Edman reagents are employed to cleave individual amino acid residues from the bound molecules for subsequent identification. With each repeated application of the reagents, the next N-terminal amino acid residue is removed. This process may be continued until an amino acid attached to the carrier is reached; although an attached amino acid can be cleaved from the next amino acid, it cannot be removed from the carrier for analysis. If additional amino acids are bound to the carrier, the sequence of amino acids residing between points of attachment may be cleaved and identified. However, when no further points of attachment exist, the unbound portion of the molecule enters solution and is thereby rendered unavailable for analysis. Hence, although multiple bonding sites impede analysis of the bound amino acid residues, a greater number of amino acids in the sample molecule will be available for sequencing than in the case of a single, early point of attachment. If attachment is random, one encounters a tradeoff between the absolute number of amino acid residues that may be successfully identified and the length of the peptide chain that will be available for analysis (see FIG. 2).

If bonding is not random, however, sensitivity to the favored amino acids will be decreased on a consistent basis. Nonrandom bonding will inhibit identification not only of the bound amino acid residues themselves, but also the terminal chain following the last favored amino acid. Random bonding assures a mixture of bound species, thereby disfavoring consistent loss of specific amino acids and a particular chain segment. Current immobilization procedures depend on specific amino acid reactivities, and therefore tend to inhibit random bonding. A general review of the present art is given in Laursen & Horn, *Coupling Methods and Strategies in Solid-Phase Sequencing*, in 25 Molecular Biology, Biochemistry and Biophysics 21 (S. Needleman, Ed., 1977).

Another limitation of many current immobilizing techniques is their utilization of carriers with functional groups that actively bond with sample molecules only within a specific pH range. This property curtails the range of polypeptides which may be analyzed, since polypeptides themselves require particular pH conditions to enter solution.

The ability of certain carriers to bond to polypeptides through photochemical means has been known for some time (see, e.g., U.S. Pat. No. 4,039,413). Because of the reactivity of the activated species, successful bonding does not require a particular pH environment. However, the procedure described in the aforementioned patent is limited by degradation of the carrier macromolecule's functional groups as a consequence of irradiation, appears to favor particular amino acids, and is not well-suited to multi-point attachment.

II. DESCRIPTION OF THE INVENTION

A. Brief Summary of the Invention

In accordance with the present invention, proteins and large polypeptides are immobilized for solid-phase sequence analysis through the formation of free radical components at the end of the carrier molecules through a photochemical process. During irradiation, the carrier's functional group is capable of random, covalent bonding to the sample. Unlike current techniques, however, the functional groups which are the subject of the present invention do not degrade as a consequence of photochemical activation. Instead, irradiation produces a triplet biradical capable of bonding to amino acid units, but which returns to its starting state upon removal of the radiation.

The reactive nature of the free radical species produced by the present invention assures that bonding to individual amino acids will be random, thereby eliminating the problem of sensitivity loss to specific amino acids, and will also remain independent of the pH of the surrounding environment. Furthermore, the absence of carrier molecule degradation as a consequence of activation permits any desired average level of bonding to take place through variation (or repetition) of the irradiation time, since continued activation will result in immobilization of a greater proportion of sample molecules as well as formation of multiple bonding sites within a given molecule. These results are obtained by utilizing particular functional groups and maintaining particular reactive conditions.

A particularly advantageous functional group, which may be utilized in conjunction with a variety of macromolecular supports, comprises aryl- or diaryl- (or substituted aryl- or diaryl-) ketone derivatives. Upon photolysis with low level ultraviolet radiation, a ketone triplet biradical is formed which inserts preferentially into carbon-hydrogen bonds present in the side chains of the sample polypeptide. Because reaction with carbon-hydrogen bonds is chemically favored over reaction with water, analyses may be performed in aqueous media, little carrier is inactivated by the solvent, and large carrier excesses are not needed. Researchers are often constrained to small amounts of sample, since many physiologically active polypeptides are present in organisms at extremely miniscule concentrations. The present invention permits utilization of minute sample quantities as a consequence of the user's ability (1) to control the degree of immobilization through variations in irradiation time, (2) to vary the pH environment of the reaction for optimum polypeptide solubility, and (3) to irradiate at wavelengths that do not damage the polypeptide structure.

B. Objects of the Invention

Accordingly, it is an object of the invention to facilitate random, covalent bonding of amino acids within polypeptides to carrier substances to allow polypeptide sequence analysis.

It is a further object of the invention to provide a photochemical method of polypeptide bonding to carrier macromolecules that does not exhibit degradation of the functional group on the carrier due to irradiation.

It is another object of the invention to allow polypeptide bonding to the carrier macromolecule over a wide range of average level of bonds per polypeptide molecule.

It is a further object of the invention to eliminate the need to maintain a specific pH in order to achieve bonding of the sample to the carrier molecules.

It is yet another object of the invention to achieve bonding of the sample to the carrier macromolecules utilizing photochemical means at wavelengths that do not damage the polypeptide structure.

C. DETAILED DESCRIPTION OF THE INVENTION

The foregoing and other and further objects of the invention will be understood more readily from the following detailed description of the invention, when taken in conjunction with the accompanying drawings, in which:

FIG. 3 depicts the fraction of amino acid available for identification analysis as a function of its position in the sample molecule and duration of irradiation when compared to diisothiocyanate (DITC) glass attachment, using a monosubstituted diaryl ketone functional group.

FIG. 4 is an illustrative sketch of apparatus for carrying out the method of the present invention.

FIG. 1 is a generalized, symbolic depiction of the photochemically activated bonding achieved by the invention described herein, whereby the carrier's active group, upon irradiation with light, bonds covalently to the side chain of an amino acid residue located on the sample polypeptide.

In a preferred embodiment of the invention described herein, the functional group is a benzophenone derivative which is insolubilized by attachment to a carrier A spacer arm is used to separate the functional group from the carrier. While the length of the spacer arm must be sufficiently long to permit free diffusion of the polypeptide without interference from the support, excessive molecular length has been found to induce unwanted reactivity among bound sample molecules.

Porous glass beads with high surface area to volume ratios provide useful supports. The advantages of utilizing porous glass beads as supports are high capacity and a large degree of rigidity. However, the invention may also be used in conjunction with a non-porous glass surface. While less efficient in terms of capacity, the small sample sizes capable of being sequenced with the Edman process prevent efficiency from becoming a limiting factor. Sequencing reactions tend to proceed faster utilizing glass surface supports; larger polypeptide molecules may also be analyzed due to absence of limiting pore size. The invention yields good random distribution of attachment sites with either type of surface.

Figure 1:
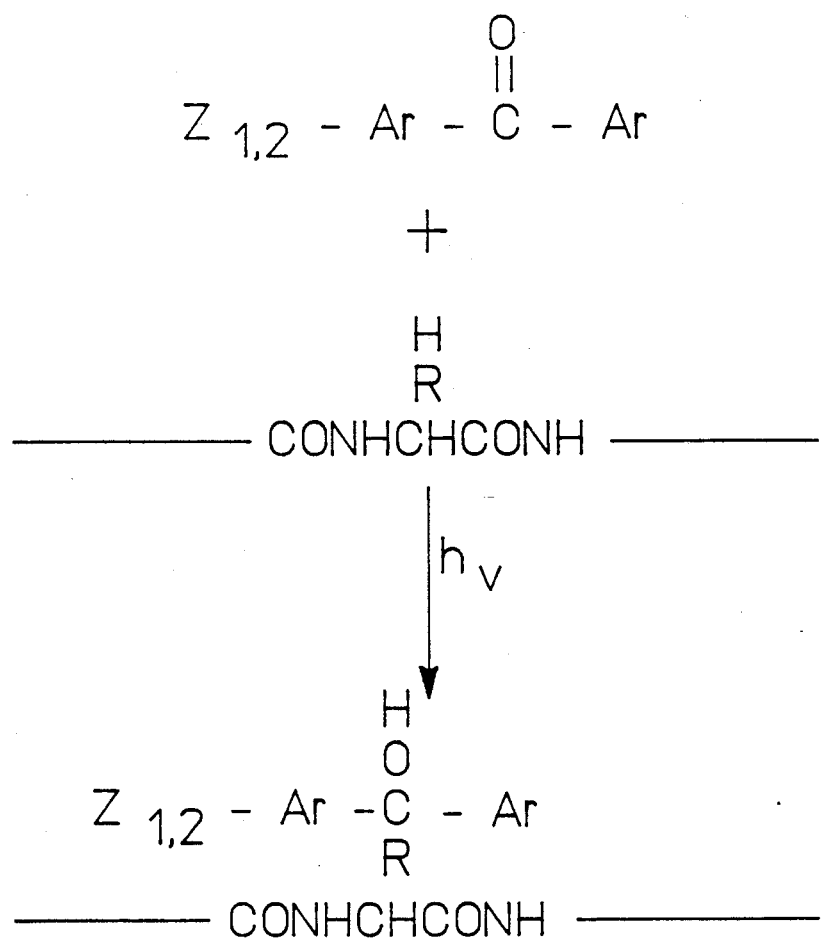
FIG. 1 illustrates the reaction of the substituted or unsubstituted aryl ketone group attached to a carrier macromolecule ($Z_{1,2}$) with the side chain of an amino acid residue.
Figure 2:
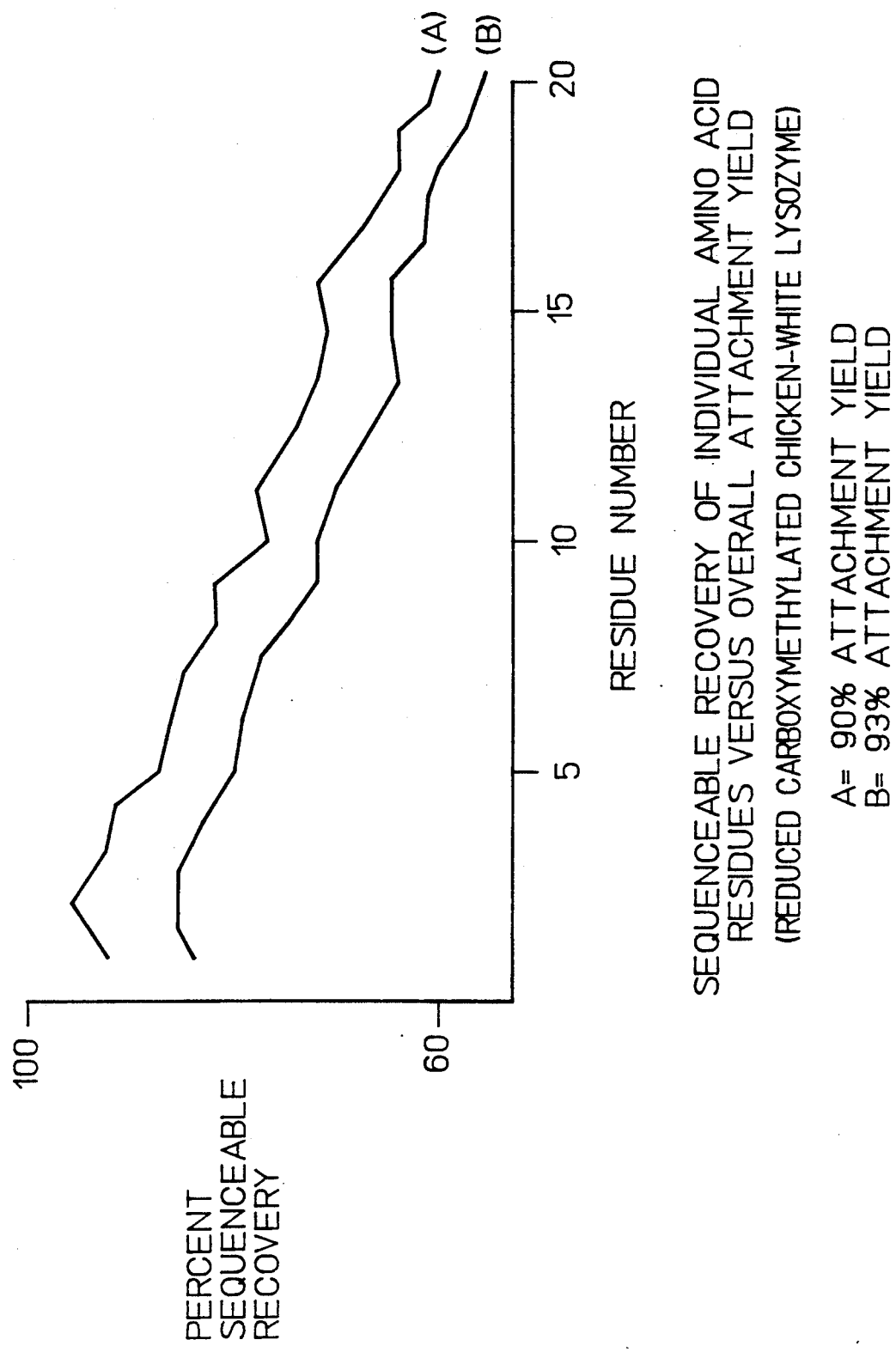
FIG. 2 shows two separate plots of the percentage of bound amino acid available for identification analysis as a function of its position in the sample molecule using a monosubstituted diaryl ketone functional group.

Preferred carrier macromolecules comprise insolubilized benzophenone derivatives bound to the carrier by a spacer arm having a molecular length of between six and twelve carbons. The appropriate wavelength of radiation to induce triplet biradical formation depends on the particular aryl species employed; the monosubstituted diaryl moiety performed optimally when irradiated with light in the 350-365 nm range. FIG. 2 illustrates differing performance levels that may be obtained at different levels of binding to the carrier. Each plot represents a different degree of sample molecule attachment to the carrier (the average number of unattached amino acids per sample molecule being expressed in percentage terms). The downward slope of the line is due to the compounding of inefficiency inherent in each degradation step, which is approximately 3% in the Edman procedure utilized.

FIG. 3 compares the fraction of amino acid available for identification analysis using the well-known technique of DITC glass attachment with the method of the present invention. Results for two periods of irradiation, 10 minutes and 40 minutes, are shown. The letters represent standard codes for amino acids. As can be seen, random bonding assures that no particular residue will suffer a significant loss of detectability as a consequence of identity or position, as is the case with the DITC method for $P_1$ and $K_{10}$. The data accompanying the 40-minute irradiation indicate that exposures of long duration are not only unnecessary but counterproductive, since excessive bonding of particular residues will lower the amount available for recovery.

FIG. 4 illustratively depicts apparatus suitable for carrying out the method of the present invention. A transparent column 10 is packed with beads 12 having bound to them an aryl- or diaryl-, or substituted aryl- or diaryl-, ketone derivative for contact with the protein or large polypeptide sample to be immobilized. The sample is initially entered by means of an inlet 14. An array of lights 16 in the form of rings 16a, 16b, 16c, etc.

surrounds the column 10 for intermittently illuminating ("flashing") the material within the column and initiating the bonding. A detector 18 on the discharge end of the column receives the sample discharged from the column, and provides an indication of the extent to which the sample is immoblized. After passing through the detector, the sample is recirculated to the imput of the column by means of a pump 20.

The detector 18 applies its output to a controller 22 having a keypad 24 for entry by the user of various parameters to control the process. For example, one such parameter is the extent of bonding to be achieved during the processing. The controller 22 in turn controls the lights 16, as well as the pump 20, to continue the processing until the desired bonding level is achieved. Other factors such as the rate of flashing, its duration, its intensity, wavelength, and the like may also desirably be set under the influence of the controller.

The invention may also be employed in conjunction with polypeptide binding techniques that do not involve completely insoluble supports. For example, reaction kinetics of particular polypeptides may favor binding to dissolved carrier molecules, which may then be precipitated for sequencing analysis.

A specific example of production and attachment of the carrier macromolecule utilizing a monosubstituted aryl ketone group, with subsequent bonding and sequencing of a representative polypeptide, is set forth in the following example given by way of illustration:

EXAMPLE

Porous glass beads (200-400 mesh, 117 angstrom pore diameter) were silated with aminopropyltriethoxysilane in acetone to yield aminopropylated glass beads. The aminopropylated beads were then refluxed with succinic anhydride in dichloromethane to yield succinamidopropyl glass beads. The succinamidopropyl beads were then coupled with p-aminobenzophenone in the presence of a carbodiimide in dimethylformamide to yield the benzophenone carrier macromolecule with a spacer arm of appropriate length.

To the support thus prepared (50 mg) was added a solution of one nanomole of cytochrome-C (C. krusei) dissolved in 100 microliters of water. The support-protein mixture was then irradiated with a long wavelength ultraviolet lamp at 365 nm for 10 minutes, and subsequently sequenced using standard Edman reagents. The results are depicted in the second row of FIG. 3. Results using a 40 minute irradiation appear in the third row.

I claim:

1. A method of immobilizing a polypeptide sample for solid-phase sequence analysis, said method comprising the steps of:
   a) providing a support macromolecule comprising a functional group sensitive to actinic radiation;
   b) introducing the polypeptide sample to said support;
   c) exposing the mixture containing said polypeptide and said support to radiation to produce a triplet biradical species in said functional group that binds directly to said polypeptide; and
   d) isolating the bound polypeptide.

2. The method of claim 1 wherein said functional group is bound to a spacer arm of sufficient molecular length to permit free diffusion of sample polypeptide molecules.

3. The method of claim 1 wherein said spacer arm has a molecular length of at least six carbon atoms.

4. The method of claim 1 wherein said functional group comprises a ketone derivative containing at least one aryl substituent.

5. The method of claim 1 wherein said at least one aryl substituent itself contains at least one substituent.

6. The method of claim 4 wherein said ketone derivative is a diaryl ketone.

7. The method of claim 6 wherein said diaryl ketone contains at least one substituent.

8. The macromolecule of claim 6 wherein said diaryl ketone is p-aminobenzophenone.

9. The method of claim 1 wherein the wavelength of said radiation is at least 350 nm.

* * * * *